United States Patent [19]
Hernandez

[11] Patent Number: 5,189,919
[45] Date of Patent: Mar. 2, 1993

[54] WELLHEAD FLUID SAMPLER

[75] Inventor: Raymond Hernandez, Andrews, Tex.

[73] Assignee: Atlantic RIchfield Company, Los Angeles, Calif.

[21] Appl. No.: 693,125

[22] Filed: Apr. 29, 1991

[51] Int. Cl.$^5$ .............................................. G01N 1/00
[52] U.S. Cl. .............................. 73/863.43; 73/863.52; 73/863.61; 73/863.86; 141/88; 222/108
[58] Field of Search ............ 73/863.42, 863.43, 863.51, 73/863.52, 863.61, 864, 864.51, 153, 863.86; 166/264, 107; 141/311 R, 324, 369, 370, 373, 86, 88; 222/108

[56] References Cited

U.S. PATENT DOCUMENTS

| | | | |
|---|---|---|---|
| 2,127,296 | 8/1938 | Holmes | 73/863.86 |
| 2,811,993 | 11/1957 | Ferdon | 141/88 |
| 4,796,677 | 1/1989 | Nice | 141/88 |
| 4,989,463 | 2/1991 | Cimaglia et al. | 73/863.86 |

Primary Examiner—Hezron E. Williams
Assistant Examiner—Michael J. Brock
Attorney, Agent, or Firm—Roderick W. MacDonald

[57] ABSTRACT

Wellhead fluid sampling apparatus comprising a closed housing with a side opening for inserting a sample receiving receptacle and a bottom aperture in sealed communication with a removable conduit that is carried by and in fluid communication with the interior of a closed container disposed below the bottom aperture.

2 Claims, 2 Drawing Sheets

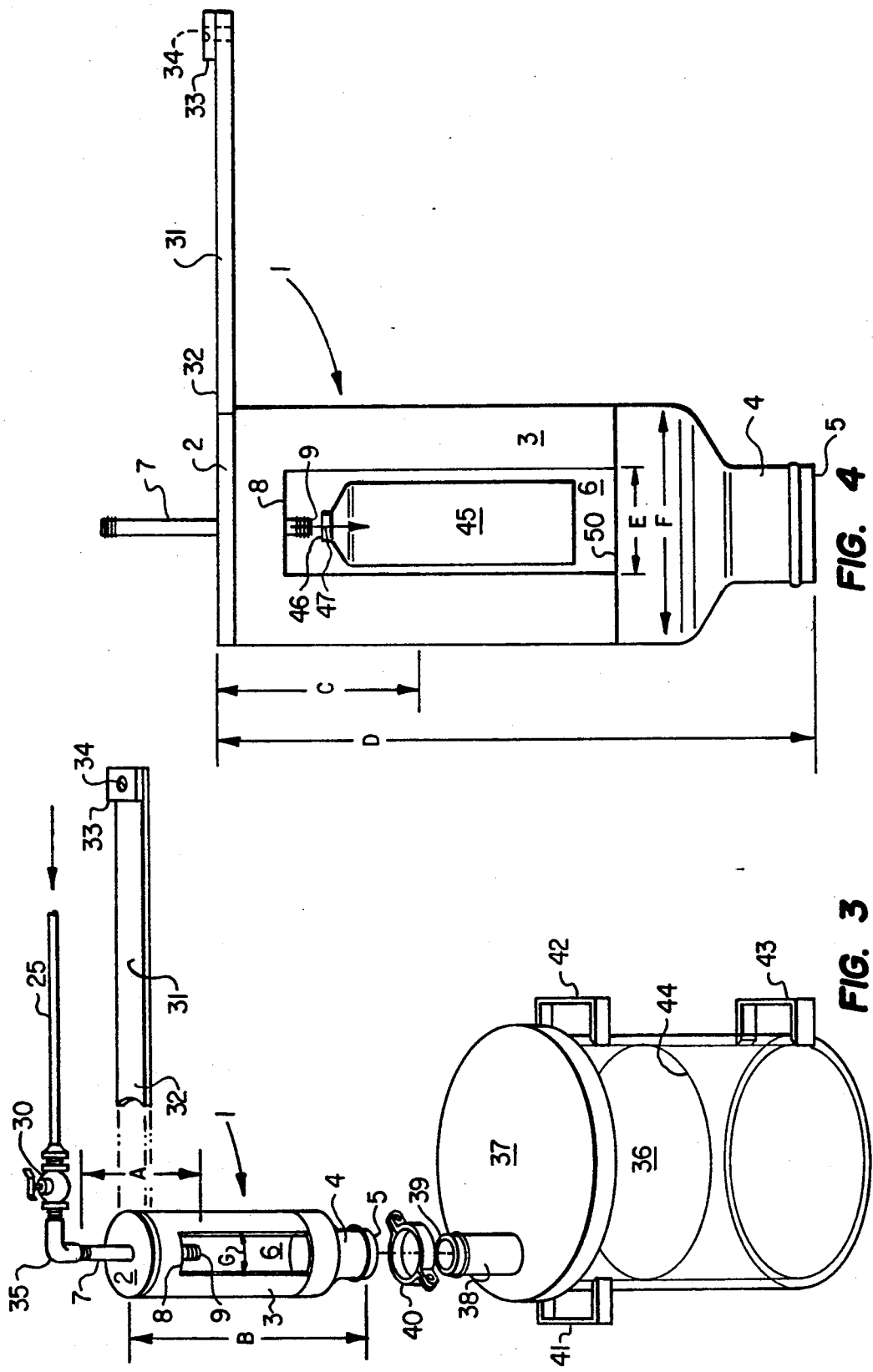

WELLHEAD FLUID SAMPLER

BACKGROUND OF THE INVENTION

Heretofore wellbores have been drilled into the earth's surface to penetrate one or more geologic formations containing a liquid mineral such as crude oil for recovery at the earth's surface. The crude oil and other gas and liquids produced from below the earth's surface rise through the wellbore and pass through a device located on the earth's surface known as a wellhead. From the wellhead the mixture of liquids which may also contain one or more gases such as natural gas, carbon dioxide, and the like pass from the wellhead through a pipe to a fluid treatment and storage area where gas can be separated from liquid, oil separated from water, and the like in a conventional and well known manner.

It is often desirable to remove a small sample of the liquid or liquids passing through the wellhead to the treatment and storage facility in order to obtain a better understanding of what is being produced from the wellbore at that particular time. Usually only a small sample, for example a pint or less of liquid volume, is necessary, and that sample may necessarily be obtained from the wellhead at any time of the day and under any type of weather conditions.

It is important to be able to draw one or more such wellhead liquid samples at any time, any number of times, and under all weather or other environmental conditions while minimizing if not eliminating the chance of spillage of such liquid on or around the wellhead during the sampling procedure. This way the wellhead is maintained and operated with minimal environmental impact.

In some sampling procedures an open topped sump is employed in the ground below the location where the sample is taken so that any drippings or spills will be collected in the sump for later removal and disposal in an environmentally acceptable manner. However, open topped sumps have the disadvantage of allowing the wind and other weather to have free access to the liquids collected in the sump. For example, volatile hydrocarbons can be carried off to the atmosphere by the wind thereby leaving a weathered hydrocarbon in the sump which is more viscous and more difficult to handle and dispose of. The sump also tends to collect dirt, sand, and other debris which mixes with the liquids in the sump and makes those liquids even more difficult to remove from the sump and otherwise handle in an expeditious manner. Further, when relying just on a sump, wind blown drippings from the sampling port can still be a problem because in a high wind the drippings can be blown beyond the surface area covered by the open sump top and can collect on the wellhead itself or be blown on to the surrounding terrain, all of which is desirably avoided since numerous samples are taken over the years of life of the well.

SUMMARY OF THE INVENTION

In accordance with this invention there is provided a sampling apparatus for use in conjunction with a wellhead which does not rely on a sump in the ground and which allows for the taking of wellhead samples under all weather conditions while still minimizing the risk of fugitive emissions of liquid during and after the sampling process.

More specifically, this invention employs an essentially closed housing means with only a very limited access aperture to the interior thereof so that a sample receptacle can be inserted into the closed interior during the sampling process. The housing is removably connected to a closed top container which collects all liquid purged before the sample is taken and any drippings that might occur after the sample has been taken. Thus, there is no reliance upon liquid reaching a sump, the collection container itself has an essentially closed top except for the access aperture to the housing, and the housing itself is essentially closed so that the wind will not carry liquid emitted from the sampling port onto surrounding equipment and terrain.

Accordingly, it is an object of this invention to provide a new and improved method for taking liquid samples from a wellbore. It is another object to provide a new and improved apparatus for minimizing environmental risk when taking wellhead fluid samples. Other aspects, objects, and advantages of the invention will be apparent to those skilled in the art from this disclosure and the appended claims.

DESCRIPTION OF THE DRAWINGS

FIG. 3 shows the apparatus of this invention including a liquid collection container and means for connecting the sampling housing to the wellhead of FIG. 2.

FIG. 4 shows the collection housing of this invention with a sample receptacle inserted therein.

DETAILED DESCRIPTION OF THE INVENTION

Figure 1:
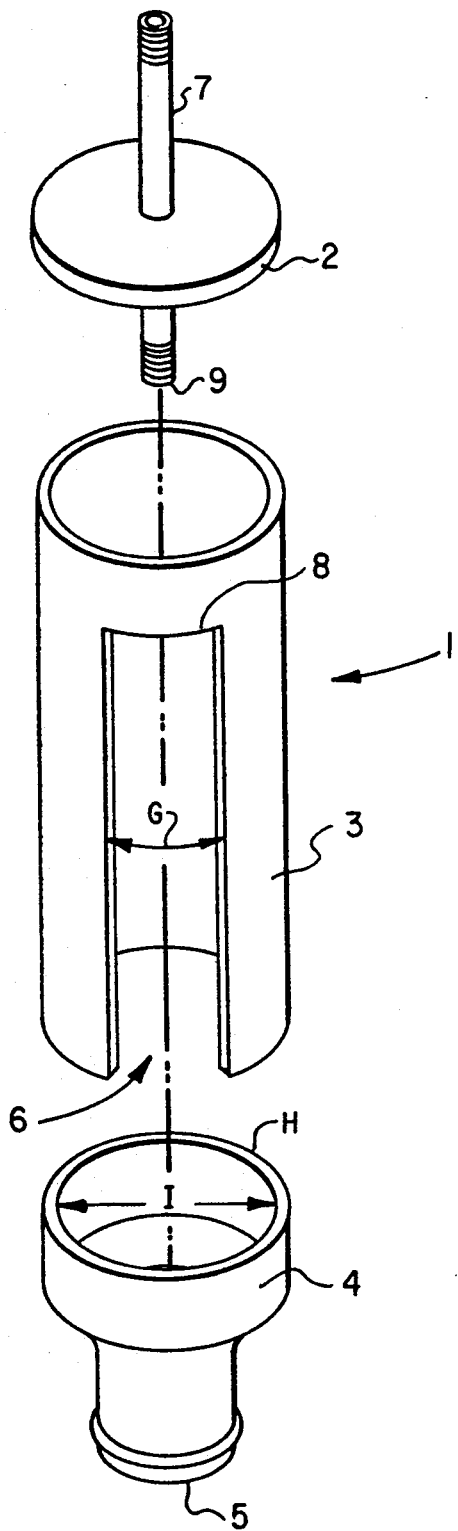
FIG. 1 shows an exploded view of the sample collection housing of this invention.

More specifically, FIG. 1 shows the sample collection housing 1 of this invention to be composed of a closed top means 2, closed upright side means 3, and a closed bottom means 4. Bottom means 4 has a first aperture 5 at the lower most end thereof so that liquid can pass from inside housing 1 to a collection container below aperture 5. Upright side section 3 has a second aperture 6 therein which is sized just large enough to allow the entry of a sample receptacle into the interior of housing 1 and below wellhead sample pipe or conduit means 7 which extends from the wellhead through closed top means 2 into the upper interior of housing 1. Second aperture 6 preferably starts at its upper most point 8 in the vicinity, for example, at or above, the lower outlet end 9 of sample conduit means 7 and terminates in the lower half of housing 1. The lateral extension G of second aperture 6 should be limited as much as possible in order to minimize the access of wind and weather to the interior of housing 1 and should be just wide enough to allow passage of a sample collection receptacle. Generally, lateral dimension G of second aperture 6 will be not greater than about twenty-five percent of the housing circumference H. When the housing is circular in configuration as shown in FIG. 1, dimension G is preferably not more than one half the diameter I of housing 1.

Figure 2:
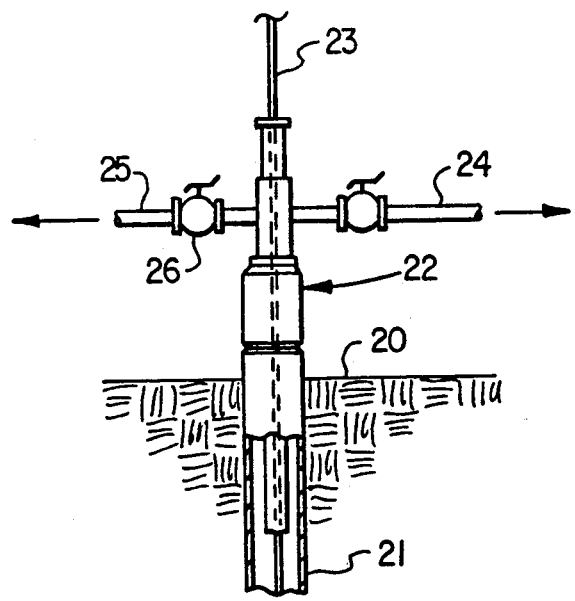
FIG. 2 shows a conventional wellhead with conventional piping for removing production fluid from the wellhead to a treatment and storage facility and additional piping for sampling fluid that is moving through that wellhead.

FIG. 2 shows the earth's surface 20 having a wellbore 21 extending down thereinto and wellbore 21 capped by a conventional wellhead 22. A pumping rod 23 reciprocates in wellbore 21 to bring crude oil and other liquids present in wellbore 21 to the earth's surface for removal by way of valved pipe 24 to a conventional treating and storage facility. Wellhead 22 also carries a conventional valved pipe 25 for removal of a fluid sample from the interior of wellhead 22 at intermittent times. Normally, only valve 26 is employed in line 25 so that opening or closing of valve 26 allows the passage of fluid from the interior of wellhead 22 to the sample receptacle.

This invention is shown in its entirety, in one embodiment thereof, in FIG. 3 starts at the outlet end of pipe 25. At such outlet end there is placed an additional valve means 30 which is then connected to pipe 7. Thus, pipe 25 is a first valved conduit means when valve 26 is included as is conventional apparatus. By this invention second valved conduit means 7 is employed which can include optional valve means 30. Optional valve means 30 is recommended in addition to conventional valve 26 in order to minimize environmental risk. For example, if only valve 26 were employed and a worker should accidentally bump the handle of valve 26 or an animal rubbing on wellhead 22 should contact the handle of valve 26, wellhead fluid could be accidentally emitted to the environment surrounding the wellhead. By employing both valves 26 and 30, the chances of accidental emission are greatly reduced. Further, by this arrangement the section of pipe 25 which extends between valves 26 and 30 can be left empty of liquid thereby minimizing the chance of a spill should that section of pipe 25 be accidentally broken by man or animal. Second conduit means 7 preferably has a length A at least about half the height B of housing 1. This is desirable in order to obtain a stabilized flow of fluid in second conduit means 7 before the fluid reaches outlet end 9 and passes into the sample receptacle. This eliminates a swirling action of the wellhead fluid as it leaves outlet 9 which can make sampling difficult and messy.

Rather than rely upon pipe 25 to carry the weight of valve 30 and housing 1 a support arm 31 of substantial strength is provided with end 32 welded or otherwise fixed to housing 1 at some convenient point along the height of that housing and opposing end 33 fixed to wellhead 22 such as by means of a bolt already existing on wellhead 22 passing through aperture 34 of end 33. By rigidly fixing housing 1 to the wellhead 22 or some other solid piece of equipment in the vicinity of wellhead 22, vibrations caused by fluid continually passing through wellhead 22 and transmitted to housing 1 by way of pipe 25 is absorbed primarily by arm 31 thereby minimizing the opportunity for such vibrations to loosen threaded connections at valve 30 and el 35 and minimizing the chance of leaks to the environment over the life of wellhead 22.

Bottom means 4 of housing 1 necks down to the size of first aperture 5. This is done so that a container means 36 with a closed but removable top means 37 can be disposed below aperture 5 with upright conduit means 38 of similar cross-sectional size and configuration as aperture 5 mated at its upper end 39 to aperture 5. Conduit means 38 provides a closed means for conducting liquid from bottom means 4 by way of conduit means 38 into the closed interior of container 36. This way any liquid spillage that occurs in the interior of housing 1 is kept in that interior and directed downwardly into the interior of container 36, such fluid being protected from exposure to wind and weather during the whole process except for the limited opening of second aperture 6. Thus, any liquid collected in container 6 is held in an essentially closed environment so that the wind cannot readily sweep volatiles away from such liquid, and dirt and other debris have only very limited access to that liquid. Upper end 39 of conduit means 38 is removably fixed to bottom means 4 in alignment with first aperture 5 by means of a removable clamp 40 which can be a conventional bolt clamp or a quick disconnect snap joint clamp as are well know in the art.

Container 36 preferably has three handles, upper, opposed handles 41 and 42 being lifting handles for removal of container 36 for transportation to a disposal site for the liquid contained therein. The third and lower handle 43 is fixed on the opposite side from conduit means 38 so that adjacent handles 42 and 43 facilitate pouring the liquid contents from the interior of container 36 through conduit means 38 at the disposal site. Container 36 can be made of any desirable material but is preferably made of a tough transparent or translucent material such as fiberglass so that an operator, upon approaching the wellhead, can readily visibly check the liquid level 44 in the interior of container 6 to determine whether that container needs to be removed to the disposal site and a new empty container put in its place. However, if high temperature liquids are to be collected and a high temperature container material used which is necessarily opaque, a sight glass or float indicator could be employed on the outside of container 36 to indicate the liquid level in the interior thereof.

FIG. 4 shows housing 1 with arm 31 fixed to top means 2 and sample receptacle 45 inserted into the interior of housing 1 so that the open top 46 of receptacle 45 is placed below outlet 9 to allow wellhead fluid to pass through the interior of pipe 25, when valves 26 and 30 are both open, and into second conduit means 7. Essentially linear fluid flow is then established in the interior of conduit 7 and the thus stabilized stream then passes into the interior of receptacle 45 as shown by arrow 47. This is the sample collection procedure. When the desired sample volume is in receptacle 45 valves 30 and 26 are closed and receptacle 45 removed from the interior of housing 1. Removal can be done essentially immediately because, due to the enclosed nature of housing 1, drips and other residual liquid that may be emitted from second conduit means 7 after valves 30 and 26 are closed and receptacle 45 removed will not become wind borne or otherwise affected by the weather but will rather pass directly downwardly through bottom means 4, aperture 5 and conduit 38 into the closed interior of container 36. Of course, if one-hundred percent surety is required which, due to the restricted size of second aperture 6 is normally not necessary, a closure means for aperture 6 can be employed as well in a manner that will be quite obvious to those skilled in the art.

As better shown in FIG. 4 outlet end 9 of second conduit means 7 preferably terminates somewhere in the upper one-third C of housing 1 and the length A (FIG. 3) of second conduit means 7 is at least one-half of the length D of housing 1. Further, as shown in FIG. 4 upper end 8 of second aperture 6 extends a little above outlet end 9 of conduit means 7 and ends at its lower end 50 in the lower half of housing 1. Further, FIG. 4 shows that the lateral extension E of second aperture 6 is no more than about two-thirds of the inside diameter F of housing means 1.

Figure 5:
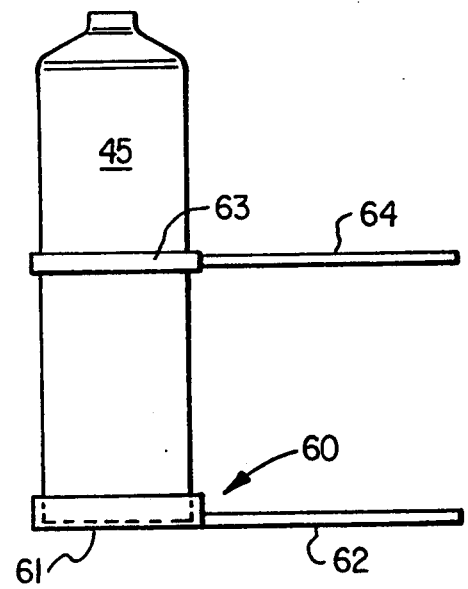
FIG. 5 shows a sample receptacle with two optional insertion devices.

Normally second aperture 6 is made sufficiently narrow so that it is difficult to insert receptacle 45 into the interior of housing 1 while holding receptacle 45 by hand. Thus, means for inserting and withdrawing receptacle 45 from the interior of housing 1 is desirable. Two such means are shown in FIG. 5, the first being a spoon-type mechanism 60 which has a cup means 61 for receiving and firmly holding the lower end of receptacle 45 together with a handle means 62 so that the operator's hand need not come in contact with receptacle 45 nor enter the interior of housing 1. Similarly, a clamp 63 can be imposed around an intermediate area of receptacle 45 which clamp also carries a handle means 64 for gripping by the operator.

Apparatus substantially as shown in FIGS. 3 and 4 has been employed on an operating wellhead wherein housing 1 was of a right-cylindrical configuration. In this embodiment second conduit means 7 was formed from ¼-inch diameter steel pipe 6-inches long with its outlet end 9 extending about 2-inches below top means 2. A length of less than 6-inches for conduit means 7 provided a swirling action of the fluid whereas a length of 6-inches or longer provides the desired stabilized sample flow. Top means 2 was welded to a 3-inch diameter, 7-inch long section of steel pipe which composed side means 3. Side means 3 was terminated by welding a 3-inch diameter swedge thereto which provided at its lower necked down end a 2-inch diameter first aperture 5. A 5-gallon fiberglass bucket of the configuration shown in FIG. 3 for container 36 was employed with an upstanding 2-inch diameter conduit 38 to match with the 2-inch diameter aperture 5. The upper end 39 of conduit 38 was fixed to aperture 5 by means of a standard 2-inch diameter victaulic coupling. The fiberglass container allowed the operator to see through the sides thereof to readily determine the liquid level 44 in the interior of the container at any time. This system allows the sampling apparatus to be purged directly down into container 36 to clear pipe 25 of residual fluid and allow a fresh, accurate fluid sample to be recovered from wellhead 22 into receptacle 45. Purging is critical to prevent the recovery of stale samples and can be done readily with the apparatus of this invention under all weather conditions without worry of environmental emission. When container 36 is full, it is disconnected by simply removing clamp 40. A removable cap is placed over opening 39 and the container hauled in this closed manner to a disposal site. The liquid content of the container readily flows, essentially in its entirety, out of the container because, by not having been exposed to the weather in an open top container and by not having collected any substantial amount of dirt or other wind-carried debris, the liquid being disposed of is neither weathered nor thickened and is easily handled in the disposal process.

Reasonable variations and modifications are possible within the scope of this disclosure without departing from the spirit and scope of this invention.

What is claimed is:

1. In wellhead fluid sampling apparatus wherein a wellhead is employed for controlling the production of fluid from a subterranean reservoir to the earth's surface, and valved first conduit means is in fluid communication with the interior of said wellhead for removing a fluid sample from said wellhead as said produced fluid passes therethrough, the improvement comprising a housing means with closed top, side, and bottom means, said bottom means having a first aperture for the removal of fluid from the interior of said housing, second conduit means in fluid communication with the interior of said first conduit means and with the upper interior of said housing means, said second conduit means being of a length which is at least one-half of the length of said housing means and sufficient to provide essentially linear flow for said fluid as it leaves said second conduit means and enters the upper interior of said housing means, a second aperture extending through said housing side means, said second aperture extending a finite distance from near the vicinity where said second conduit means terminates in the interior of said housing means toward said bottom means, said second aperture being of a width just sufficient to allow passage of a sample receptacle through said second aperture and into the interior of said housing means below said second conduit means so that fluid leaving said second conduit means flows into said receptacle when held in the interior of said housing means, said second aperture width being a minor portion of the circumference of said side means and no more than about two-thirds of the inside diameter of said housing means so that said receptacle is essentially enclosed by said side means when in the interior thereof, and closed container means removably connected to said housing means in fluid communication with said first aperture to receive and hold any fluid not retained in said receptacle.

2. The apparatus according to claim 1 wherein said housing means is essentially cylindrical and said second conduit means terminates in the upper one-third of said housing means.

* * * * *